United States Patent
Swart et al.

(10) Patent No.: US 10,667,986 B2
(45) Date of Patent: Jun. 2, 2020

(54) APPARATUS FOR TREATING THE HUMAN OR ANIMAL BODY WITH MECHANICAL STROKES

(71) Applicant: STORZ MEDICAL AG, Tägerwilen (CH)

(72) Inventors: Stephan Gerhard Swart, Moers (DE); Carlo Di Maio, Duisburg (DE); Ulrich Piontkowski, Bietigheim-Bissingen (DE); Pavel Novak, Stetten (CH); Johannes Manfred Schulz, Tägerwilen (CH)

(73) Assignee: STORZ MEDICAL AG, Tagerwilen (CH)

( * ) Notice: Subject to any disclaimer, the term of this patent is extended or adjusted under 35 U.S.C. 154(b) by 723 days.

(21) Appl. No.: 14/865,742

(22) Filed: Sep. 25, 2015

(65) Prior Publication Data

US 2016/0089296 A1    Mar. 31, 2016

(30) Foreign Application Priority Data

Sep. 26, 2014  (DE) ................... 20 2014 010 461 U
Sep. 26, 2014  (DE) ................... 20 2014 010 463 U
Sep. 26, 2014  (EP) ................... 14 186 623

(51) Int. Cl.
*A61H 9/00*    (2006.01)
*A61H 23/04*   (2006.01)
*A61B 17/225*  (2006.01)
*A61B 17/22*   (2006.01)

(Continued)

(52) U.S. Cl.
CPC ....... *A61H 23/04* (2013.01); *A61B 17/22004* (2013.01); *A61B 17/2251* (2013.01); *A61H 23/008* (2013.01); *A61B 2017/00544* (2013.01); *A61H 2023/002* (2013.01); *A61H 2201/0153* (2013.01); *A61H 2201/123* (2013.01); *A61H 2201/1246* (2013.01)

(58) Field of Classification Search
CPC .............. A61H 23/04; A61H 23/008; A61H 2201/1246; A61H 2201/123; A61H 2201/0153; A61H 2023/002; A61B 17/22004; A61B 17/2251; A61B 2017/00544

See application file for complete search history.

(56) References Cited

U.S. PATENT DOCUMENTS 4,498,464 A    2/1985   Morgan, Jr.
4,549,535 A   10/1985   Wing
(Continued)

FOREIGN PATENT DOCUMENTS

DE    197 25 477 A1      12/1998
DE    10 2004 042 895 A1  6/2005
DE    20 2014 004 070 U1  7/2014

OTHER PUBLICATIONS

EPO Search Report dated Mar. 13, 2015.

*Primary Examiner* — Quang D Thanh
(74) *Attorney, Agent, or Firm* — Wood, Phillips, Katz Clark & Mortimer

(57) ABSTRACT

The invention relates to an apparatus for treating a human or animal body by mechanical strokes, wherein an applicator for being placed on the patient's body surface has a basically oblique front area portion in an angle between 30° and 60° to the stroke direction.

17 Claims, 4 Drawing Sheets

(51) Int. Cl.
   *A61H 23/00*   (2006.01)
   *A61B 17/00*   (2006.01)

(56) References Cited

U.S. PATENT DOCUMENTS

| | | | | |
|---|---|---|---|---|
| 5,843,005 | A * | 12/1998 | Chubinsky | A61H 7/003 |
| | | | | 601/15 |
| 7,503,923 | B2 * | 3/2009 | Miller | A61H 1/008 |
| | | | | 173/114 |
| 2002/0177795 | A1 | 11/2002 | Frye | |
| 2005/0015028 | A1 * | 1/2005 | Luettgen | A61H 19/34 |
| | | | | 601/72 |
| 2005/0131461 | A1 * | 6/2005 | Tucek | A61H 1/008 |
| | | | | 606/239 |
| 2009/0221940 | A1 | 9/2009 | Marlinghaus et al. | |
| 2011/0054367 | A1 * | 3/2011 | Schulz | A61H 23/008 |
| | | | | 601/46 |
| 2014/0350438 | A1 * | 11/2014 | Papirov | A61B 17/225 |
| | | | | 601/2 |

* cited by examiner

APPARATUS FOR TREATING THE HUMAN OR ANIMAL BODY WITH MECHANICAL STROKES

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD OF THE INVENTION

The present invention relates to an apparatus for treating the human or animal body by applying strokes to the body surface. Below, for a simplification, reference is made to the body of a patient which is preferably human.

BACKGROUND OF THE INVENTION

In the prior art, different apparatuses of the basic type described are known. DE 197 25 477 C relates to such an apparatus for instance, wherein a shockwave is initiated by a collision of a pneumatically accelerated striking member or projectile with an impact body or applicator resting initially, wherein the shockwave can be coupled into the body of the patient when a front area of the applicator is placed on the patient's body at the time of the collision. As regards the history of its development, this type of apparatus results from lithotripsy apparatuses which can be used for transferring such a shockwave onto a kidney stone or the like for a disintegration, for instance via a long rod-like probe at the front area of the applicator.

Therein, an emphasis is on the shockwave generated by the collision, which can be more or less comparable to an actual shockwave generated by a classical typically focusing lithotripsy apparatus having for instance a piezoelectric or inductive actuator and a focusing on a stone. Such shockwaves can have a leading edge with a width in the region of a few μs and an amplitude in a lower double-digit MPa region (for instance 2 μs and 15 MPa measured 1 cm in front of the front area). In the document cited however, it is emphasized that the macroscopic movement of the applicator's center, which cannot be prevented as such physically, shall be kept rather small because it is considered as disadvantageous.

As a second example, reference is made to DE 20 2004 011 323 U and US 2011/0054367 A1 having a comparable content. There, an apparatus which is comparable as regards its technical design is described, the elastic mounting of the applicator in the housing being however adapted for a larger movement of the applicator's center ("travel"). There, it is emphasized that a therapeutic effect can be caused also or mainly by the actual macroscopic strokes (namely as a result of the travel), which also depends from the indication.

In general, the present invention relates to apparatuses of that type, namely regarding the application of shockwaves as well as regarding the application of "macroscopic strokes" of the applicator to the body surface.

Therein, the invention is to solve the problem to provide such an apparatus with further application possibilities on the body surface of the patient.

SUMMARY OF THE INVENTION

The problem is solved by an apparatus as disclosed herein. Therein, according to the invention, the applicator has an oblique front area portion amounting to at least 30% of a front area of the applicator, which lies in front with respect to the stroke direction, the front area portion pointing outwards obliquely with respect to the stroke direction therein having an angle to the stroke direction (see 17 in FIGS. 2a, 2b, 4a and 4b) between 30° and 60°.

Accordingly, an oblique area is a substantial part of the front area of the applicator. Therein, "oblique" means an angle to the stroke direction between 30° and 60° wherein the stroke direction corresponds to a longitudinal direction of the apparatus in many cases practically relevant (for instance in case of apparatuses having a design according to the documents cited).

The "front area" of the applicator shall contain that parts of the outer area which point forward and can be placed on the body surface of the patient, wherein "pointing forward" means that a local surface normal has a component in direction of the stroke direction (and does not lie opposite or perpendicular thereto). Thus, an area lying parallel to the stroke direction does not belong to the front area and an area pointing rearwards does neither.

Finally, the oblique area shall be a substantial portion of the front area, amounting to at least 30% of the area of the latter wherein a portion of (in the following order increasingly preferred) 35%, 40%, 45%, 50%, 55%, 60%, 65%, 70% is increasingly preferred. Therein, the areas are considered in their actual three-dimensional extension which means not as projected areas in a viewing direction from the front for instance.

The inventors found out that it can be convenient to place the applicator at the patient's body surface obliquely with respect to the stroke direction. In particular, this relates to treatments wherein the apparatus is moved on the body surface. Then, the apparatus can be held better and can be moved over the body surface in a manner better controllable and more comfortable for the therapist. Therein, in particular, tissue portions below the skin can be massaged and/or pushed along in front of the apparatus while being treated at the same time with the strokes and (to a different extent as the case arises) shockwaves. Therein, the apparatuses conventionally known having an applicator with a more or less flat front area are rather inadequate, because they can only be placed on the skin surface in a more or less perpendicular orientation of the apparatus with respect to the body surface.

The apparatus for generating the strokes of the applicator can be provided in various designs, in particular also by a direct admission of the applicator by an electromagnetic mechanism or a pressure pulse. However, preferably, an accelerated projectile as known from the cited documents is used for a collision with the applicator, which results in rather intense and (in terms of the velocity of the applicator) fast strokes and allows a use of shockwaves at the same time or even primarily. Again, the projectile can be also accelerated in different ways, in particular also electromagnetically, wherein a pneumatic admission of the projectile as described in the documents cited is also preferred here.

The term "applicator" does not necessarily relate to a one-piece part. It is also possible and also preferred depending on the application that the projectile hits a first part for instance, which transmits the stroke and/or the shockwave onto a second applicator part contacting the skin of the patient. Occasionally, an intermediate piece between the applicator and the projectile is referred to in the prior art; insofar, a multi-part applicator is referred to, wherein the two applicator parts can be firmly attached, which is not necessary however.

As mentioned above, a comparably large travel of the applicator can be required, wherein in the present case the apparatus is preferably provided such that strokes with a travel above 1 mm can be reached, as already described in US 2011/0054367 A1.

The oblique area mentioned (the oblique front area portion in the claims) is preferably not concave, namely is flat or convex (which also comprises a combined flat-convex shape) for allowing a good contact to the skin or body surface and a concentrated application of force when the apparatus is put in place.

According to a further embodiment, the oblique front area portion and preferably the front area as a whole are free of edges. This means that the radii of curvature there shall be 2 mm at minimum, preferably 3 mm at minimum, 4 mm at minimum or even 5 mm at minimum. This is also advantageous in view of an application of the apparatus by the therapist with a certain force and/or a pushing movement; therein, the therapist needs to take less care of the orientation of the apparatus and/or a possible irritation or injury of the patient by edges, for instance edges at the rim of the applicator area being actually applied.

Further, the oblique front area portion as a whole has preferably an area of at least 1.5 cm$^2$ at minimum wherein the following lower limits are increasingly preferred in the following order: 1.75 cm$^2$ and finally 2.0 cm$^2$. With an increasing area, a larger tissue region can be covered and the force of the stroke and/or the applying force of the therapist can be distributed more broadly. Therein, the values mentioned above relate to the whole oblique front area wherein, depending on the application, only part of the latter is used, for instance in case of a front area mainly arranged on two sides only that half which currently points to the patient.

Further, it is preferred that a large portion of the oblique front area portion is comparably flat. This does not relate to being free of edges, but to which extent the area contains curvatures. At least 80% of the area portion should have a radius of curvature of at least 5 mm, preferably at least 6 or even 7 mm. In certain embodiments having an oblique front area portion being basically flat, even a lower limit of 10 mm, 20 mm, 30 mm, 40 mm or even 50 mm can be preferred.

A further aspect of the invention relates to the symmetry of the front area portion with respect to the stroke direction (which is usually also the length direction of the apparatus). In the prior art, as far as known, applicators are described having a basically rotationally symmetric geometry. However, in the present case, a geometry is preferred which is not completely rotationally symmetric. In principle, a certain symmetry, namely a symmetry with a limited number of symmetry operations is possible and even advantageous as shown by the exemplary embodiments, a fourfold symmetry being preferred at maximum, a threefold or even twofold symmetry being further preferred. For illustration, this means that in case of a symmetry with a certain number of symmetry operations, an according number of oblique front area portions corresponding each other symmetrically, namely being transferable into each other, are present. Thus, in case of a twofold symmetry, two oblique areas are present, which can be used in the same manner, wherein three oblique areas are present in case of a threefold symmetry. One of the embodiments shows a version being not rotationally symmetrical, but having a mirror symmetry.

In a comparable context, it is further preferred that the oblique front area portion is somehow concentrated on a portion of a rotational angle around the stroke direction. For illustration, this means that the oblique front area portions shall, looking onto the applicator in a direction opposite to the stroke direction (namely from the front), be not distributed evenly around the applicator but be concentrated on 4, 3, 2 or even only one oblique area.

The applicators known consist usually of stainless steel. In the present case, metals can be used in general, in particular stainless steel. Further metallic materials can for instance be aluminium or titanium, both having a comparably low mass density which enables rather lightweight applicators. This can be advantageous since a stronger acceleration and larger travel thus are possible at a given geometry of the applicator, which can be desired in the present case. Further, titanium is characterized by a high mechanical loadability, being appropriate for applications with a comparably high velocity of the projectile and/or mass of the projectile. Since titanium is further characterized by a good physiological tolerance, it can also be an advantageous applicator material independently of the loadability.

Further, ceramics, see the application no, 08 003 840.9/EP 2 095 843, and synthetic materials can be used. In comparison to stainless steel, those are also advantageous in view of having a smaller mass density. Further, the heat conductivity is smaller than in case of metals so that the patient perceives the applicator as being warmer subjectively. This applies in particular for synthetic materials. Synthetic materials are in particular of interest when the coupling of the shockwave is less important, because there can be certain losses in the wave conductance in comparison to the aforementioned materials, at least when a larger thickness of the synthetic material is assumed. The same applies for wood.

BRIEF DESCRIPTION OF THE DRAWINGS

Below, the invention is explained in further details by means of two exemplary embodiments wherein the individual features can, in the scope of claim 1, be also relevant for the application independently of each other and in other combinations.

DETAILED DESCRIPTION OF THE INVENTION

Figure 1:
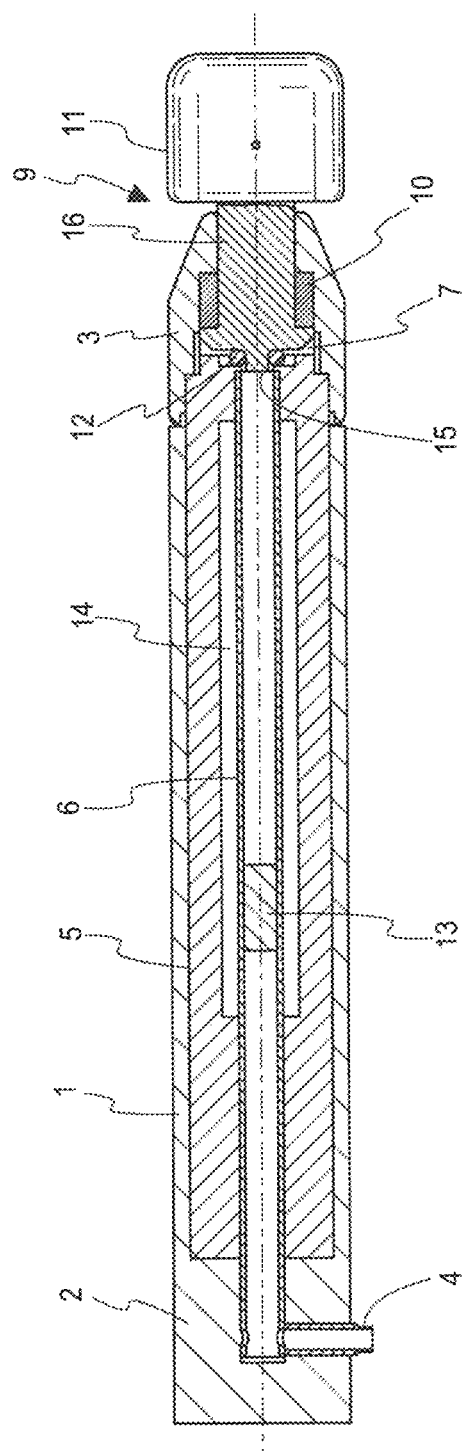
FIG. 1 shows a shockwave apparatus as a first exemplary embodiment of the invention, having an applicator shown in FIG. 2 in further detail.

FIG. 1 shows a first embodiment of the invention. It is an apparatus for coupling strokes and unfocused (so-called radial) mechanical shockwaves into the human or animal body.

A tube piece 1 forms a housing, namely together with an air inlet cap 2 pointing away from the body in the application and being integrated with the tube piece 1 and an applicator cap 3 pointing towards the body in the application. The air inlet cap 2 comprises a compressed air supply 4 for a pneumatic supply. In a manner known as such, a valve controlled by a control unit, in particular a magnetic valve, is connected to this compressed air supply 4 via a pneumatic supply line, the valve coupling compressed air pulses in a constant repetitive cycle between for instance 1 Hz and 50 Hz via the compressed air supply. The valve is not shown and can also be integrated into the shown apparatus itself.

Further, the apparatus is an apparatus to be held by hand by an operating personnel, being connected via the aforementioned pneumatic line to a base station with the control unit and the compressor and being placeable on the patient manually. It is used for treating soft tissue, in particular muscles and fasciae.

In the housing, a guiding tube 6 is held by an inset 5, whose end being distal to the body in the application is terminated by the air inlet cap 2 and communicates with the compressed air supply 4 there. The end of the guiding tube 6 which is proximal to the body in the application ends in a part of the inset 5, the part projecting into the applicator cap 3, namely ends briefly before the local end of the inset 5 and before an inner space 7 in the applicator cap 3.

In the inner space 7 which merges into an applicator opening proximal to the body in the application, a first part of an applicator 9 is received which is hatched in FIG. 1. Via an elastic tube element 10 made of an elastomer, it rests on a radial collar. An end 15 of the applicator 9, oriented to the side distal to the body and containing the impact area, rests on the inset 5 via an O-ring 12, namely at a front face surrounding the end of the inset 5 mentioned above. Therein, the O-ring 12 is located between this front face and a collar of the applicator 9. Therein, the applicator opening provides a guidance of the applicator 9 with a movability in the length direction and secures it obliquely to the length direction. The axial displaceability is only limited by the deformability of the elastomer element 10 and can be significantly above 1 mm with respect to the remaining apparatus in case of an apparatus driven by air.

As a further part, the applicator 9 comprises the element 11 being not hatched, which forms the actual applicator applied to the skin. The applicator 9 can be exchanged by unscrewing the applicator cap 3.

In the adjacent region of the guiding tube 6, a projectile 13 is inserted, which is in contact with the applicator 9 in FIG. 1. It fits therein with a minor clearance (with respect to the guiding tube and the basically cylindrical geometry of the projectile 13). The projectile 13 can be moved to-and-fro in the guiding tube 6 by pressure gradients in the air column in the guiding tube 6 in front of and behind the projectile (namely at the right and the left of the projectile 13 in FIG. 1), in particular it is accelerated onto the applicator 9, Therefore, it is accelerated from an initial position (not shown) on the left in FIG. 1 by a pressure pulse through the compressed air supply 4 and hits the applicator 9 with a front area pointing towards the applicator 9, namely hits a impact area 15 thereof pointing away from the body.

In addition to a rebound after the collision, the backward motion of the projectile 13 is supported by air flowing back from an accumulation chamber 14 surrounding the guiding tube 6 within the inset 5. Into the accumulation chamber, the air is displaced during the acceleration of the projectile 13 towards the impact body 9 and it is compressed therein. When the pressure is released by the magnetic valve, the space behind the projectile being vented therein, the projectile 13 is moved back into the initial position. In addition or alternatively, this can also occur by a pressurization of the accumulation chamber 14 or of another air volume at a side of the projectile 13 proximal to the body. The end of the guiding tube 6 being distal to the body in the application, ends at a magnet holder for the projectile 13.

In FIG. 1, a part 16 of the applicator 9 being thinner radially with respect to the longitudinal axis of the apparatus is drawn hatched and the remaining part 11 has no hatching. If the hatched part 16 would be terminated by for instance a slightly convex boundary line, this would be the conventional shape of an applicator. With such a shape, the applicator 9 would be primarily adapted for being placed vertically on the body surface of the patient. According to the invention, the applicator 9 is enlarged towards the patient's body, namely by the part 11 without hatching. Seen in a direction perpendicular to the longitudinal direction, the latter has the shape shown in FIG. 1 and it has the shape shown in FIG. 2b in the second direction perpendicular to the first direction, Therein, the applicator 9 is shown approximately in an appropriate ratio to the remaining apparatus in FIG. 1 but is enlarged in FIG. 2. As an example, it has a vertical extension in FIG. 1 of 30 mm and a length (in the longitudinal direction) of 25 mm, wherein the radii of curvature amount to 5 mm at a side proximal to the patient's body in the transition 20 of the two boundary areas in the projection according to FIG. 1. However, in FIG. 2b, at the same length (in the longitudinal direction) of 25 mm, the extension perpendicularly thereto is smaller, amounting to 15 mm, wherein a semi-circular rounding at the side proximal to the patient's body in the projection of FIG. 2b has a radius of 7.5 mm.

In the third representation c of FIG. 2, the looking direction is along the longitudinal direction of the stroke direction 17 onto the front part 11 of the applicator 9, wherein a rectangular basic form is visible (with the aforementioned edge lengths of 30 mm and 50 mm), the corners however being rounded having a radius of curvature of 5 mm respectively. A central longitudinal axis 17' extends in the stroke direction (see FIGS. 2(c) and 4(c)). The fourth representation d illustrates the shape of the applicator in a perspective view.

Figure 2A:
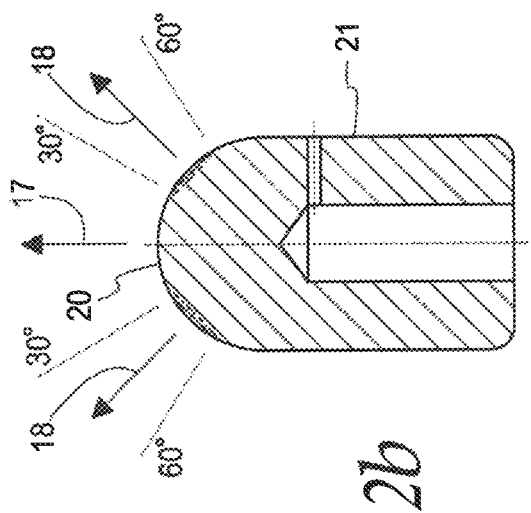
FIG. 2 shows a front part of the applicator of the apparatus of FIG. 1 in the same viewing direction as in FIG. 1 (but upright) in the representation part a, in a sectional view with a viewing direction turned around the longitudinal axis by 90° in the representation part b, looking in the length direction of the apparatus in a further representation c and finally in a perspective view in the representation part d.
Figure 2B:
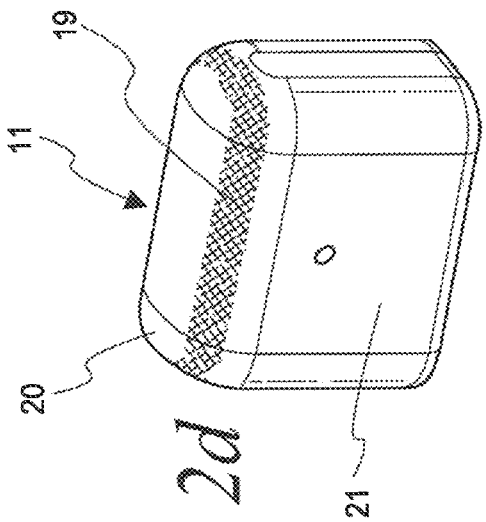
Figure 2C:
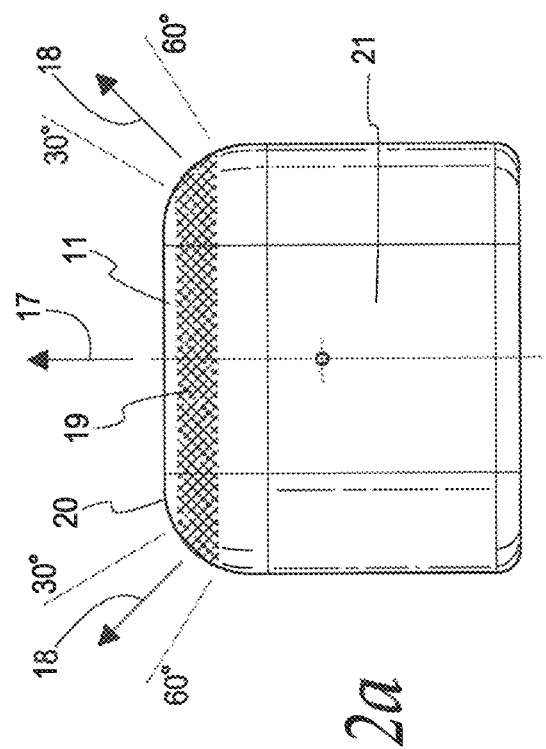
Figure 2D:
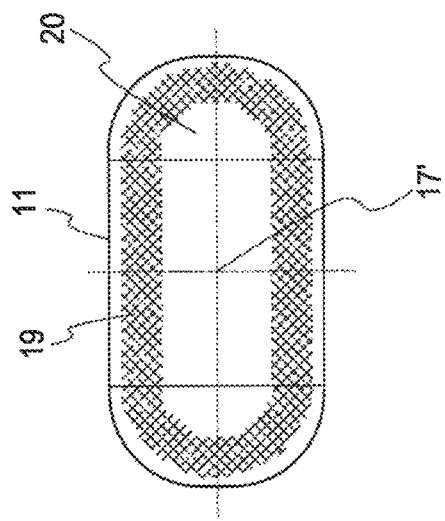

The front area of the front part 11 of the applicator 9 has a semi-cylindrical shape in the perspective view of FIG. 2b, the corners however being rounded in two projection planes with radii of curvature of 5 mm, see the Figures. Neglecting the additional roundings, this semi-cylindrical shape has a portion of one third with angles of the respective local area portions (or the normal thereto) to the longitudinal direction between 30° and 60° (see the 30° and 60° lines at the upper right and left of FIG. 2a); considering the further roundings, this portion is slightly higher. The corresponding angle sectors and area portions are indicated by radii and hatchings. FIG. 2b shows already that the oblique front area portion 19 lies in the defined angle region between 30° and 60° (see the 30° and 60° lines at the upper right and left of FIG. 2b), amounting to one third of the front area semi-circular in this section. Due to the roundings, in the front view of FIG. 2c, there is also a correspondingly oblique front area portion 19 at the side (in FIG. 2c to the left and the right) so that the relative portion as a whole is one third approximately and above 30%, thus.

With respect to the longitudinal direction, it has a two-fold symmetry and can be placed on the body surface of the patient with both front area portions having a width of 30 mm and corresponding a quarter of a cylinder, respectively. In case of a contact angle of 45° used therein approximately, the area portions having an angle between 30° and 60° to the longitudinal direction are of a particular interest. The front area of the applicator appears particularly suited for being swept or pushed over the body surface due to the relative portion of the front area portions in combination with the particularly wide shape (30 mm) in comparison to the prior art and due to the significant rounding. For the same reasons, strokes (which are in direction 17 as indicated on FIGS. 2a, 2b, 4a and 4b) having comparably large travel values above 1 mm can be coupled comparably gently in a wide spread manner into the body.

As a whole and in particular in its front part 11, the applicator 9 has a two-fold symmetry with respect to the longitudinal direction (and two mirror symmetries in addition wherein the symmetry planes intersect in the longitudinal direction), the whole front area of the applicator being convex therein. All radii of curvature occurring amount to at least 5 mm and the oblique front area has an area of about 2.5 cm² in total. Since only a side of the applicator is applied to the body in a typical application, for instance the portion of the front area pointing to the upper left in FIG. 2b, only a part of the applicator is in contact to the skin. Taking the lateral rounded regions (on the right and the left in FIG. 2c) not contacting the skin into account, the contact area should be in a range between 1.0 to 1.2 cm².

In a viewing direction of the longitudinal direction, the oblique front area portion is located on the two long sides of the rounded rectangle.

The applicator 9 can be for instance made of aluminium titanium, synthetic material, ceramics or wood.

As regards its removability, the parts 11 and 16 can preferably be firmly connected, for instance by a plug or screw connection. The parts 11 and 16 can be made of different materials.

Alternatively, the front part 11 of the applicator could be also provided at an applicator comparable to that depicted in FIG. 4 of the aforementioned US 2011/0054367 A1, wherein its widest extension would be comparable to the diameter of the apparatus also in this case. Then, it could be pulled off towards the front through the opening in the applicator cap after the latter has been disengaged and further parts have been removed.

Figure 3:
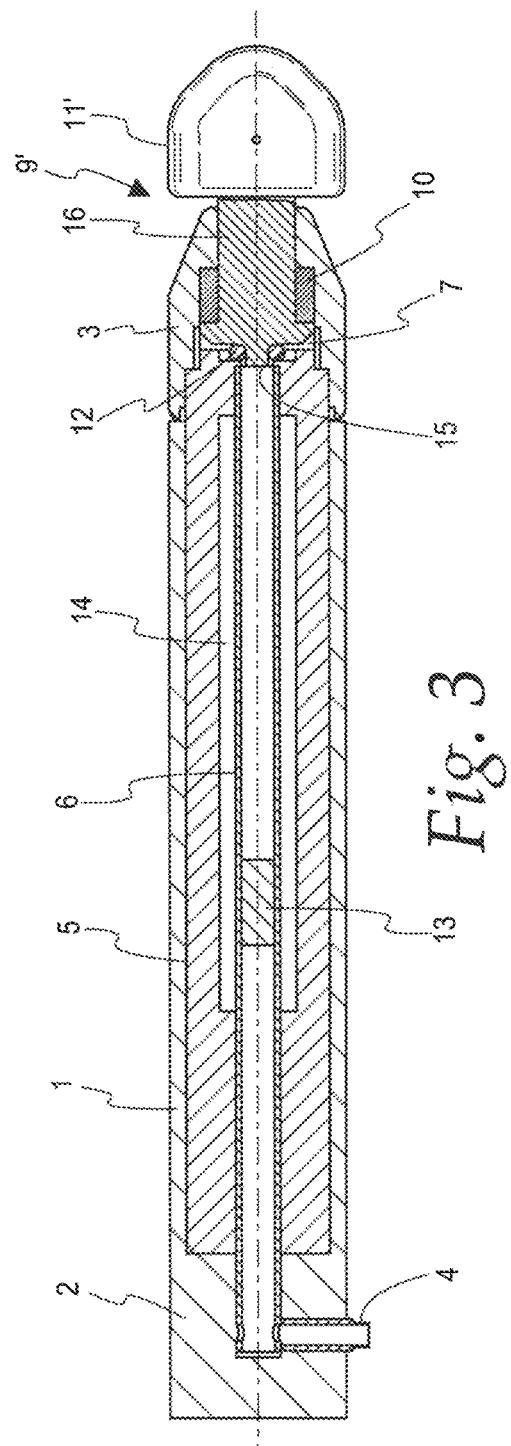
FIG. 3 shows a second embodiment in analogy to FIG. 1, but having another applicator shown in FIG. 4.

FIGS. 3 and 4a to d show a second alternative embodiment, the latter Figures showing only the front applicator part 11' which is shown in FIG. 3 at an apparatus as in FIG. 1 or which could also be provided at an apparatus of the cited US document. Apart from the different applicator shape, the individual representations of FIG. 4 correspond to the individual representations of FIG. 2, wherein the width of the applicator 11' according to FIG. 4b amounts to 20 mm (instead of 15 mm in FIG. 2b).

Figure 4B:
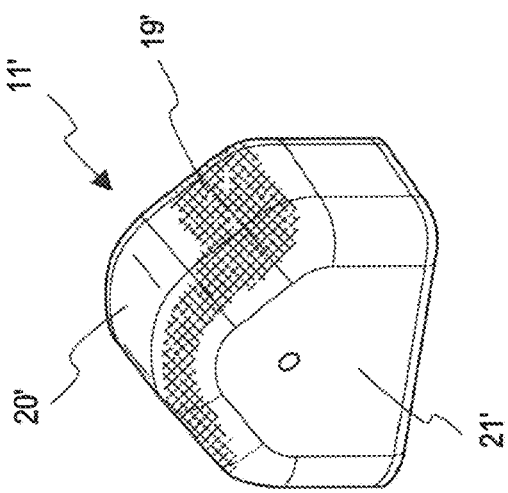
FIG. 4 shows a front part of the applicator of the apparatus of FIG. 3 in the same viewing direction as in FIG. 3 (but upright) in the representation part a, in a sectional view with a viewing direction turned around the longitudinal axis by 90° in the representation part b, looking in the length direction of the apparatus in a further representation c and finally in a perspective view in the representation part d.
Figure 4A:
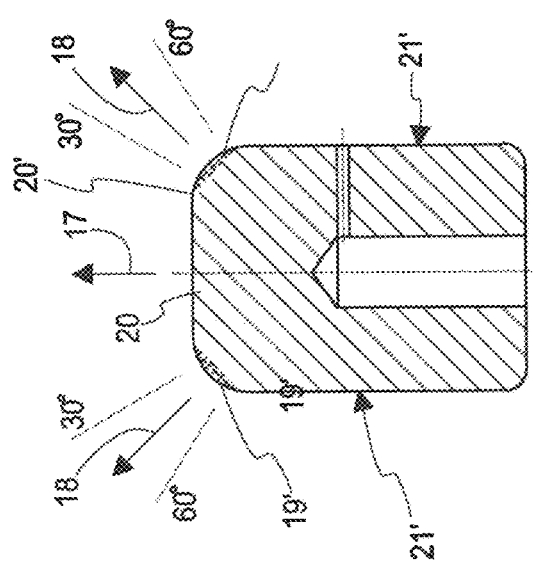
Figure 4D:
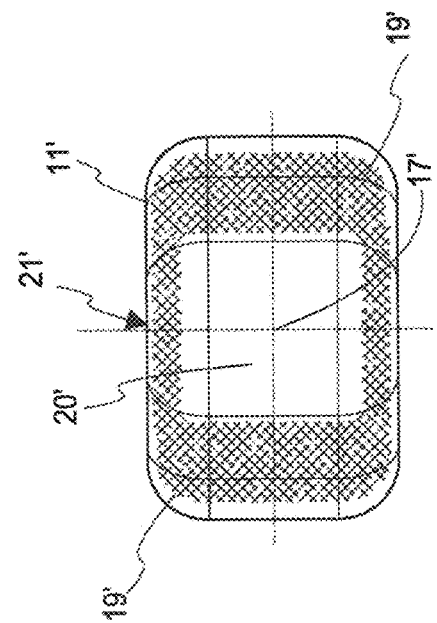
Figure 4C:
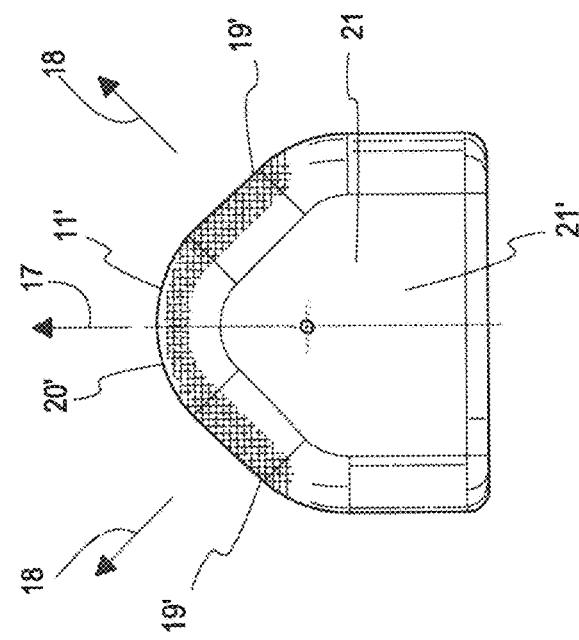

In FIG. 4a, comparably large oblique front area portions having an angle of 45° to the longitudinal direction are visible, wherein these portions extend into the transitions between the oblique areas amongst themselves and between the oblique areas and areas extending parallelly to the longitudinal direction of the apparatus, the transitions being rounded with a radius of 10 mm. In FIG. 4b, the semi-cylindrical shape of FIG. 2b is missing; instead, a rectangle having radii of curvature of 5 mm at the corners on top is provided here. Thus, the oblique front area portions consist mainly of the areas being plane and having an angle of 45° to the longitudinal direction in FIG. 4, with a minor part of the adjacent rounding as hatched. This results in an area of around 2 cm² approximately, wherein the oblique front area portions are located at an angle region of about 140° roughly (with respect to the perspective in the longitudinal direction). Apart from that, reference is made to the explanations above referring to the first embodiment, including the limited rotational symmetry around the center axis 17' which extends in the direction of the stroke direction 17. In both cases, a preferred material is the synthetic material POM (a high-molecular thermoplastic currently referred to as acetal).

The invention claimed is:

1. An apparatus for treating a human or animal body, comprising:
    an applicator adapted to be placed on said body from outside said body,
    a housing in which said applicator is held, and
    an apparatus adapted to generate strokes of said applicator with respect to said housing in a stroke direction so that said strokes are adapted to be imparted into said body when said applicator is placed on said body,
    wherein said applicator has a continuous front area having an oblique front area portion which amounts to at least 30% of said continuous front area of said applicator, lying in front with respect to said stroke direction, said oblique front area portion pointing outwards obliquely with respect to said stroke direction,
    wherein said oblique front area portion has a rotational symmetry which is twofold at maximum with respect to a central longitudinal axis extending in said stroke direction, said oblique front area portion lies in a defined angle region having an angle between 30° and 60° relative to said central longitudinal axis, and said oblique front area portion is free of edges with all radii of curvature being 2 mm at a minimum.

2. The apparatus according to claim 1, wherein said apparatus adapted to generate said strokes comprises a projectile and an accelerator adapted to accelerate said projectile in such a way that said projectile hits said applicator and generates said strokes.

3. The apparatus according to claim 1, wherein said oblique front area portion is planar or convex but is not concave.

4. The apparatus according to claim 1, wherein said oblique front area portion has an overall area of 1.5 cm² at minimum.

5. The apparatus according to claim 1, wherein said oblique front area portion comprises a portion of at least 80% of said continuous front area of said applicator and a radius of curvature of said oblique front area portion is 5 mm at minimum.

6. The apparatus according to claim 1, wherein said oblique front area portion is formed on four sides at a maximum.

7. The apparatus according to claim 1, wherein a part of said applicator, which is adapted for being placed on said body, is made of one of metal, synthetic material, ceramics and wood.

8. The apparatus according to claim 1, wherein said applicator is adapted for a travel of said strokes of 1 mm at minimum in said stroke direction relatively to said housing.

9. The apparatus according to claim 1, wherein
said continuous front area of said applicator comprises a semi-cylindrical shape, and
said applicator
has a substantially rectangular basic shape in a viewing direction opposite to said stroke direction,
has a semi-circular shape corresponding to said semi-cylindrical shape in a first viewing direction perpendicular to said stroke direction and
has a substantially rectangular shape in a second viewing direction perpendicular to said stroke direction.

10. The apparatus according to claim 1, wherein
said continuous front area of said applicator further comprises a second oblique front area portion, each oblique front area portion having an angle of 30° to 60° relative to said central longitudinal axis with a rounded transition in between,
two areas parallel to said stroke direction are provided between said oblique front area portions, and
said applicator
has a substantially rectangular basic shape in a viewing direction opposite to said stroke direction,
has a rounded-acute shape corresponding to said oblique front area portions with said rounded transition in a first viewing direction perpendicular to said stroke direction and
has a substantially rectangular basic shape in a second viewing direction perpendicular to said stroke direction.

11. The apparatus according to claim 1, wherein said applicator has a pair of spaced flat side areas extending parallel to said stroke direction wherein said continuous front area of said applicator extends between said pair of spaced flat side areas.

12. An apparatus for treating a human or animal body, comprising:
an applicator adapted to be placed on said body from outside said body,
a housing in which said applicator is held, and
an apparatus adapted to generate strokes of said applicator with respect to said housing in a stroke direction so that said strokes are adapted to be imparted into said body when said applicator is placed on said body,
wherein said applicator has an oblique front area portion which amounts to at least 30% of a front area of said applicator, lying in front with respect to said stroke direction, said oblique front area portion pointing outwards obliquely with respect to said stroke direction, and
wherein said front area of said applicator comprises a semi-cylindrical shape, and
said applicator
has a substantially rectangular basic shape in a viewing direction opposite to said stroke direction,
has a semi-circular shape corresponding to said semi-cylindrical shape in a first viewing direction perpendicular to said stroke direction and
has a substantially rectangular shape in a second viewing direction perpendicular to said stroke direction, and
wherein said oblique front area portion has a rotational symmetry which is twofold at maximum with respect to a central longitudinal axis extending in said stroke direction.

13. The apparatus of claim 12, wherein said oblique front area portion is free of edges whereby all radii of curvature of said oblique front area portion are 2 mm at minimum.

14. The apparatus according to claim 12, wherein said oblique front area portion comprises a portion of at least 80% of said front area of said applicator and a radius of curvature of said oblique front area portion is 5 mm at minimum.

15. An apparatus for treating a human or animal body, comprising:
an applicator adapted to be placed on said body from outside said body,
a housing in which said applicator is held, and
an apparatus adapted to generate strokes of said applicator with respect to said housing in a stroke direction so that said strokes are adapted to be imparted into said body when said applicator is placed on said body,
wherein said applicator has an oblique front area portion which amounts to at least 30% of a front area of said applicator, lying in front with respect to said stroke direction, said oblique front area portion pointing outwards obliquely with respect to said stroke direction, and
wherein said oblique front area portion has a rotational symmetry which is twofold at maximum with respect to a central longitudinal axis extending in said stroke direction;
wherein said front area of said applicator further comprises a second oblique front area portion, each oblique front area portion having an angle of 30° to 60° relative to a central longitudinal axis extending in said stroke direction with a rounded transition in between with two areas parallel to said stroke direction provided between said oblique front area portions, and
said applicator
has a substantially rectangular basic shape in a viewing direction opposite to said stroke direction,
has a rounded-acute shape corresponding to said oblique front area portions with said rounded transition in a first viewing direction perpendicular to said stroke direction and
has a substantially rectangular basic shape in a second viewing direction perpendicular to said stroke direction.

16. The apparatus of claim 15, wherein each of said oblique front area portions is free of edges whereby all radii of curvature of each of said oblique front area portions are 2 mm at minimum.

17. The apparatus according to claim 15, wherein each of said oblique front area portions comprises a portion of at least 80% of said front area of said applicator and a radius of curvature of each of said oblique front area portions is 5 mm at minimum.

* * * * *